(12) United States Patent
Damiano, Jr. et al.

(10) Patent No.: US 7,918,847 B2
(45) Date of Patent: Apr. 5, 2011

(54) METHOD AND ASSOCIATED SYSTEM FOR THE INTERVENTIONAL TREATMENT OF ATRIAL FIBRILLATION

(75) Inventors: Ralph James Damiano, Jr., St. Louis, MO (US); Richard Bruce Schuessler, Ballwin, MO (US)

(73) Assignee: Washington University, St. Louis, MO (US)

( * ) Notice: Subject to any disclaimer, the term of this patent is extended or adjusted under 35 U.S.C. 154(b) by 886 days.

(21) Appl. No.: 11/214,256

(22) Filed: Aug. 29, 2005

(65) Prior Publication Data

US 2007/0049816 A1    Mar. 1, 2007

(51) Int. Cl.
*A61B 5/05* (2006.01)
*A61B 18/20* (2006.01)

(52) U.S. Cl. ............. 606/14; 606/41; 128/898; 600/407
(58) Field of Classification Search ............... 606/41, 606/1, 33, 15, 32; 600/407, 585, 411
See application file for complete search history.

(56) References Cited

U.S. PATENT DOCUMENTS

| | | | | |
|---|---|---|---|---|
| 4,357,946 | A * | 11/1982 | Dutcher et al. ............ | 607/131 |
| 5,613,937 | A * | 3/1997 | Garrison et al. ............ | 600/201 |
| 5,954,665 | A * | 9/1999 | Ben-Haim ................... | 600/515 |
| 6,558,382 | B2 * | 5/2003 | Jahns et al. .................. | 606/41 |
| 6,663,622 | B1 | 12/2003 | Foley et al. | |
| 6,669,694 | B2 * | 12/2003 | Shadduck ..................... | 606/41 |
| 6,932,813 | B2 | 8/2005 | Thompson et al. | |
| 7,681,579 | B2 * | 3/2010 | Schwartz ..................... | 128/898 |
| 2001/0034488 | A1 * | 10/2001 | Policker et al. .............. | 600/515 |
| 2002/0087183 | A1 * | 7/2002 | Boyd et al. ................... | 606/190 |
| 2003/0167056 | A1 * | 9/2003 | Jahns et al. ................... | 606/41 |
| 2004/0181139 | A1 * | 9/2004 | Falwell et al. ............... | 600/374 |
| 2005/0203502 | A1 * | 9/2005 | Boveja et al. ................ | 606/32 |
| 2007/0032826 | A1 * | 2/2007 | Schwartz ...................... | 607/2 |
| 2007/0043285 | A1 * | 2/2007 | Schwartz ..................... | 600/407 |
| 2007/0043296 | A1 * | 2/2007 | Schwartz ..................... | 600/463 |

OTHER PUBLICATIONS

Chen et al., Preoperative Atrial Size Predicts the Success of Radiofrequency Maze Procedure for Permanent Atrial Fibrillation in Patients Undergoing Concomitant Valvular Surgery, Jun. 2004, Chest, 125:2129-2134.*

Mien-Cheng Chen, Jen-Ping Chang, and Hsueh-Wen Chang, "Preoperative Atrial Size Predicts the Success of Radiofrequency Maze Procedure for Permanent Atrial Fibrillation in Patients Undergoing Concomitant Valvular Surgery", Chest, 2004; 125; pp. 2129-2134.*

(Continued)

*Primary Examiner* — Henry M Johnson, III
*Assistant Examiner* — Jeffrey B Lipitz
(74) *Attorney, Agent, or Firm* — Thompson Coburn LLP

(57) ABSTRACT

A method for treatment of atrial fibrillation includes utilizing mathematical analysis, e.g., logistic regression, on a collection of variables selected from the group including effective refractory period, wavelength, tissue area, tissue weight, maximum tissue width, minimum tissue width, and average tissue width to design a set of lesions that would make an atria fibrillation-proof. Preferably, the most preferred variables are tissue area, effective refractory period, and conduction velocity. This is preferably an electrophysiologically-customized procedure that is preferably minimally invasive, which could include transvenous or port access, either off or on bypass to create the set of lesions that render an atria fibrillation-proof based on the mathematical analysis of selected variables. Long linear lesions are created from a variety of energy sources as well as surgical techniques. Preferably, there are fixation and marking mechanisms utilized.

10 Claims, 12 Drawing Sheets

OTHER PUBLICATIONS

Rahul N. Doshi, MD et al., Relation Between Ligament of Marshall and Adrenergic Atrial Tachyarrhythmia, 1999, pp. 876-883, American Heart Association, Inc., U.S.

Rodney H. Falk, M.D., Atrial Fibrillation; New England Journal of Medicine, Apr. 5, 2001, pp. 1067-1078, vol. 344, No. 14, Massachusetts Medical Society, U.S.

Sydney L. Gaynor, MD et al., Surgical treatment of atrial fibrillation: Predictors of late recurrence, The Journal of Thoracic and Cardiovascular Surgery, Jan. 2005, pp. 104-111, Washington University School of Medicine, U.S.

Alan S. Go, MD et al., Prevalence of Diagnosed Atrial Fibrillation in Adults National Implications for Rhythm Management and Stroke Prevention: the AnTicoagulation and Risk Factors in Atrial Fibrillation (ATRIA) Study, JAMA, May 9, 2001, pp. 2370-2375, vol. 285, No. 18, American Medical Association, U.S.

Sunil M Prasad, MD et al., The Cox maze III procedure for atrial fibrillation: Long-term efficacy in patients undergoing lone versus concomitant procedures, The Journal of Thoracic and Cardiovascular Surgery, Dec. 2003, pp. 1822-1827, Washington University School of Medicine, U.S.

Norbert Wiener et al., The Mathematical Formulation of the Problem of Conduction of Impulses in a Network of Connected Excitable Elements, Specifically in Cardiac Muscle, ,Archos. Inst. Cardiol,. 1946, pp. 205-265, Mexico.

Walter E. Garrey, The Nature of Fibrillary Contraction of the Heart—Its Relation to Tissue Mass and Form, American Journal of Physiology, 1914, vol. 33, pp. 397-414, U.S.

Gordon K. Moe, On the Multiple Wavelet Hypothesis of Atrial Fibrillation, Arch. Int. Pharmacodyn., 1962, CXL, No. 1-2, pp. 183-188, New York, U.S.

Gordon K. Moe, MD et al., A computer model of atrial fibrillation, American Heart Journal, vol. 67, No. 2, Feb. 1964, pp. 200-220, New York, U.S.

Maurits A. Allessie et al., Experimental Evaluation of Moe's Multiple Wavelet Hypothesis of Atrial Fibrillation, Cardiac Electrophysiology and Arrhythmias, D. P. Zipes and J. Jalife, 1985 (New York: Grune & Stratton), pp. 265-276, U.S.

Karen Konings TS et al., Arrhythmias/Innervation/Pacing: High-Density Mapping of Electrically Induced Atrial Fibrillation in Humans, vol. 89(4), Apr. 1994, pp. 1665-1680, U.S.

James L. Cox et al., The Development of the Maze Procedure for the Treatment of Atrial Fibrillation, Seminars in Thoracic and Cardiovascular Surgery, vol. 12, No. 1, pp. 2-14, 2000, St. Louis, Missouri, U.S.

Yoshio Kosakai, Treatment of Atrial Fibrillation Using the Maze Procedure: The Japanese Experience, Seminars in Thoracic and Cariovascular Surgery, vol. 12, No. 1, pp. 44-52, 2000, Perth, Australia.

Richard B. Schuessler et al., Cholinergically Mediated Tachyarrhythmias Induced by a Single Extrastimulus in the Isolated Canine Right Atrium, Circulation Research, vol. 71, pp. 1254-1267, 1992, Dallas, Texas, U.S.

Philip V. Bayly et al., Estimation of Conduction Velocity Vector Fields From Epicardial Mapping Data, IEEE Transactions on Biomedical Engineering, vol. 45, No. 5, May 1998, pp. 563-571, New York,U.S.

Rodney H. Falk, MD, Etiology and Complications of Atrial Fibrillation: Insights From Pathology Studies, American Journal of Cardiology, 1998; vol. 82 pp. 10N-17N, New Jersey, U.S.

T. Lewis, Theory of Circus Movement and Its Application to Pure Flutter, pp. 319-324, The Mechanisms and Graphical Registration of the Heart Beat, London, UK, Shaw and Sons, Chapter 26, pp. 319-324, 1925.

* cited by examiner

| Tissue Geometry of the RA and LA | | | |
|---|---|---|---|
| Variables | RA | LA | P Value |
| Surface area | 4068.3 ± 494.7 mm² | 3851.9 ±522.2 mm² | P=0.027 |
| Weight | 7.61 ± 1.6 g | 8.23 ±0.70 g | P=0.002 |
| Maximum widths | 91.8 ± 4.4 mm | 91.2 ±4.6 mm | P=0.518 |
| Minimum widths | 75.7 ± 4.4 mm | 78.9 ±7.1 mm | P=0.012 |
| Average widths | 83.4 ± 4.3 mm | 85.1 ±4.7 mm | P=0.057 |
| Maximum height | 56.7 ± 5.9 mm | 51.9 ±2.9 mm | P<0.001 |
| Minimum height | 38.7 ± 3.9 mm | 41.1 ±7.0 mm | P=0.044 |

FIG. 4

| ERP, CV, and Wavelength in the RA and LA | | | |
|---|---|---|---|
| Variable | RA | LA | P Value |
| Whole preparation (before ablations) | | | |
| ERP no ACh | 126.9 ± 23.9 ms | 139.0 ±33.7 ms | P= 0.152 |
| ERP with ACh | 23.8 ± 10.7 ms | 31.2 ±8.1 ms | P= 0.003 |
| All sections combined | | | |
| ERP no ACh | 120.5 ± 27.8 ms | 141.2 ±36.3 ms | P< 0.001 |
| ERP with ACh | 32.7 ± 17.1 ms | 33.9 ±9.1 ms | P= 0.527 |
| Conduction velocity | 0.943 ± 0.048 mm/ms | 0.99 ±0.095 mm/ms | P= 0.001 |
| CV SD | 0.279 ± 0.043 mm/ms | 0.26 ±0.036 mm/ms | P< 0.001 |
| Whole preparation (before ablations) | | | |
| Maximum CV | 1.486 ± 0.016 mm/ms | 1.48 ±0.03 mm/ms | P= 0.001 |
| Minimum CV | 0.300 ± 0.105 mm/ms | 0.41 ±0.14 mm/ms | P< 0.001 |
| All sections combined | | | |
| Maximum CV | 1.457 ± 0.064 mm/ms | 1.46 ±0.09 mm/ms | P= 0.849 |
| Minimum CV | 0.396 ± 0.165 mm/ms | 0.48 ±0.17 mm/ms | P= 0.001 |
| Wavelength no ACh | 112.77 ± 28.9 mm | 145.73 ±46.7 mm | P< 0.001 |
| Wavelenght with ACh | 30.4 ± 15.1 mm | 33.9 ±11.6 mm | P= 0.154 |
| ACh indicates acetylcholine. | | | |

FIG. 5

Univariable Logistical Regression

| Variable | P Value | McFadden Rho Squared | Constant Coefficient | Variable Coefficient | N |
|---|---|---|---|---|---|
| ERP | <0.001 | 0.513 | 3.182943 | -0.083691 | 397 |
| Wavelength | <0.001 | 0.486 | 2.851849 | -0.082362 | 397 |
| Area | <0.001 | 0.055 | -1.837034 | 4.29E-4 | 397 |
| Weight | <0.001 | 0.048 | -1.677815 | 0.191325 | 397 |
| Width max | <0.001 | 0.060 | -1.985283 | 0.020934 | 397 |
| Width min | <0.001 | 0.058 | -1.780872 | 0.022293 | 397 |
| Width avg | <0.001 | 0.058 | -1.891795 | 0.021654 | 397 |

Results from univariable analysis are presented above using the equation for the probability of $AF = e^{(x)}/[1+\exp^{(x)}]$, where x=constant + coefficent(variable). Variable units are: ERP (ms), wavelenght (mm), area (mm²), weight (g), width and height (mm), velocity and velocity STD (mm/ms), maximum conduction velocity (max CV, mm/ms), minimum conduction velocity (min CV, mm/ms), and atria (left vs right).

FIG. 8

TABLE 4. Multivariable Logistical Regression

| X=constant+ $\beta_0$(variable 1)+ $\beta_1$(variable 2) | P Value | McFadden Rho Squared |
|---|---|---|
| 1.209-8.219E-2(ERP)+8.802E-4(area) | <0.001, <0.001 | 0.590 |
| 0.701-8.801E-2(WL)+9.12E-4(area) | <0.001, <0.001 | 0.569 |
| 1.167-8.31E-2(ERP)+4.38E-2(width avg) | <0.001, <0.001 | 0.594 |
| 0.9866-8.135E-2(ERP)+4.112E-2(width max) | <0.001, <0.001 | 0.593 |
| 0.3459-7.943E-2(WL)+4.497E-2(width max) | <0.001, <0.001 | 0.581 |
| 1.540-0.084(ERP)+0.388(weight) | <0.001, <0.001 | 0.583 |
| -20.953-7.919E-2(ERP)+16.292(max CV) | <0.001, 0.003 | 0.539 |

Results from the multivariable logistical regression are presented above using the equation for the probability of $AF=e^{(x)}/[1+exp^{(x)}]$. The value for x is defined in the left column of the table. Variable units are: ERP (ms), wavelenght (mm), area ($mm^2$), weight (g), width (mm), mean conduction velocity (mean CV, mm/ms), and maximum conduction velocity(max CV, mm/ms). WL indicates wavelength.

FIG. 10

METHOD AND ASSOCIATED SYSTEM FOR THE INTERVENTIONAL TREATMENT OF ATRIAL FIBRILLATION

BACKGROUND OF THE INVENTION

Atrial fibrillation ("AF") is the most common sustained cardiac arrhythmia in the world. There are thought to be over 2.3 million Americans that are living with atrial fibrillation.[1] In 1914, Garrey[2] theorized that a critical mass of tissue was necessary to maintain atrial fibrillation.[3] Garrey[2] theorized that multiple wavelets circulated through the atria around transitory and shifting lines of block, activating the atria in a chaotic manner that sustained atrial fibrillation. Using computer modeling, researchers[4,5] demonstrated that multiple wavelet reentry theoretically could be used as a mechanism to sustain atrial fibrillation. Others subsequently confirmed multiple wavelet reentry as a cause of atrial fibrillation in studies in animals and humans.[6,7] Weiner and Rosenbluth[8] introduced the concept of wavelength, defined as the product of refractory period and conduction velocity ("CV"), which represents the minimum path length needed for reentry in sustained atrial fibrillation.

There has been developed a Maze procedure that divides the atrium into a maze and prevents macro circuit reentry, while still allowing for normal sinus activation of the atrium. Recent long-term follow-up data demonstrated a success rate of greater than ninety percent (90%). Although a successful procedure, there still remains a subset of patients for which this procedure does not cure of atrial fibrillation.

Kosakai[11] examined their operative experience and found a decreasing success rate with increasing preoperative atrial sizes. When the left atria ("LA") diameter was less than forty-five (45) millimeters, the success rate in conversion to normal sinus rhythm ("NSR") after the Maze procedure was one hundred percent (100%). When the diameter was over eighty-seven (87) millimeters, there was a zero percent (0%) success rate for conversion to normal sinus rhythm after the Maze procedure. It is hypothesized that the Maze procedure does not divide the atria into small enough sections to prevent atrial fibrillation in patients with an enlarged atria.

At the present time, all surgical operations, including the Maze procedure, e.g., Maze III procedure and the Maze IV procedure, and pulmonary vein isolation, are based on encircling anatomic landmarks. The theory behind these procedures was that atrial fibrillation originates either from the pulmonary veins or is due to reentry around the mitral or tricuspid annuli, pulmonary veins, or the inferior or superior vena cava. The Maze III procedure was developed in an attempt to stop the multiple macroreentrant circuits felt to be responsible for atrial fibrillation. Recently, other investigators have pointed to the importance of pulmonary veins as triggers for atrial fibrillation. This has resulted in attempts to anatomically isolate the pulmonary veins. Unfortunately, current surgical approaches to the treatment of atrial fibrillation have had success rates that have ranged from ten percent (10%) to ninety percent (90%). There is a need for a treatment having a much higher and constant success rate. The present invention is directed to overcoming one or more of the problems set forth above and could be applied to any catheter-based or surgical intervention.

SUMMARY OF INVENTION

These are merely some of the innumerable aspects of the present invention and should not be deemed an all-inclusive listing of the innumerable aspects associated with the present invention. These and other aspects will become apparent to those skilled in the art in light of the following disclosure and accompanying drawings.

An aspect of the present invention is a method for the treatment of atrial fibrillation. This method includes utilizing mathematical analysis, e.g., logistic regression, on a collection of variables selected from the group including effective refractory period, wavelength, tissue area, tissue weight, maximum tissue width, minimum tissue width, and average tissue width to design a set of lesions that would make an atria fibrillation-proof. Preferably the most preferred variables to analyze are tissue area, effective refractory period, and conduction velocity.

Another aspect of the present invention is to utilize an image-guided, electrophysiologically-customized procedure. This procedure is preferably minimally invasive, which could include transvenous or port access, either off or on bypass to create the set of lesions that render an atria fibrillation-proof based on mathematical analysis of selected variables.

Still another aspect of the present invention is creation of long linear lesions from the group including, but not limited to, radio frequency, microwave, laser, ultrasonic, thermal, chemical, mechanical, or cryogenic energy.

Yet another aspect of the present invention is a fixation mechanism for the atrial epicardium that is preferably a unipolar device that may include suction, however, suture, clamping or balloon inflation may also be utilized.

Still yet another aspect of the present invention is a marking mechanism to delineate a precise lesion width. The marking mechanism is proposed to be a dye that would be infused through the device to make it clearly visible to the observer, however, other marking devices may include clips, absorbable strips, felt, staples, and so forth.

In another aspect of the present invention, a device to divide the posterior pericardial reflections is disclosed. This device may include a deflectable handle that could retract the heart and also may include a cautery, ultrasound, or scissors device to divide the pericardium.

These are merely some of the innumerable aspects of the present invention and should not be deemed an all-inclusive listing of the innumerable aspects associated with the present invention. These and other aspects will become apparent to those skilled in the art in light of the following disclosure and accompanying drawings.

BRIEF DESCRIPTION OF DRAWINGS

For a better understanding of the present invention, reference may be made to the accompanying drawings in which:

FIG. 4 illustrates a table of geometric parameters for a left atria and a right atria with a standard deviation for each value and a P value to provide a probability that replication of the experiments would yield the same conclusion;

FIG. 5 illustrates a table of effective refractory periods, conduction velocities, and wavelength in a left atria and a right atria for a whole preparation and all sections combined with a standard deviation for each value and a P value to provide a probability that replication of the experiments would yield the same conclusion;

FIG. 8 illustrates a table of univariable logistical regression for a variety of variables such as effective refractory period, wavelength, tissue area, tissue weight, maximum tissue width, minimum tissue width, and average tissue width;

FIG. 10 illustrates a table of multivariable logistical regression for a variety of constants.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as to obscure the present invention.

In this new method for the treatment of atrial fibrillation, the anatomic-based approach to the arrhythmia will be discarded, and replaced with a procedure based on the electrophysiological and geometrical characteristics of the atrial tissue in each individual patient. This procedure is individualized to the particular atrial geometry.

Referring now to an illustrative, but nonlimiting experimental procedure to determine the importance of atrial geometry and an effective refractory period based on the ability of the atrium to be able to sustain atrial fibrillation. A set of twenty animals (n=20), e.g., normal mongrel dogs, weighing between 20 and 30 kilograms, were intravenously anesthetized with 7.5 milligrams/kilogram propofol, intubated, and placed on a positive pressure respirator with 2% to 3% isoflurane for anesthesia throughout the procedure. A median sternotomy was performed, the heart was cradled in the pericardium, and the azygous vein was ligated and divided. The interatrial groove was dissected, separating the left atria and right atria. Two dissection protocols were used to isolate the left atria and right atria.

Figure 1:
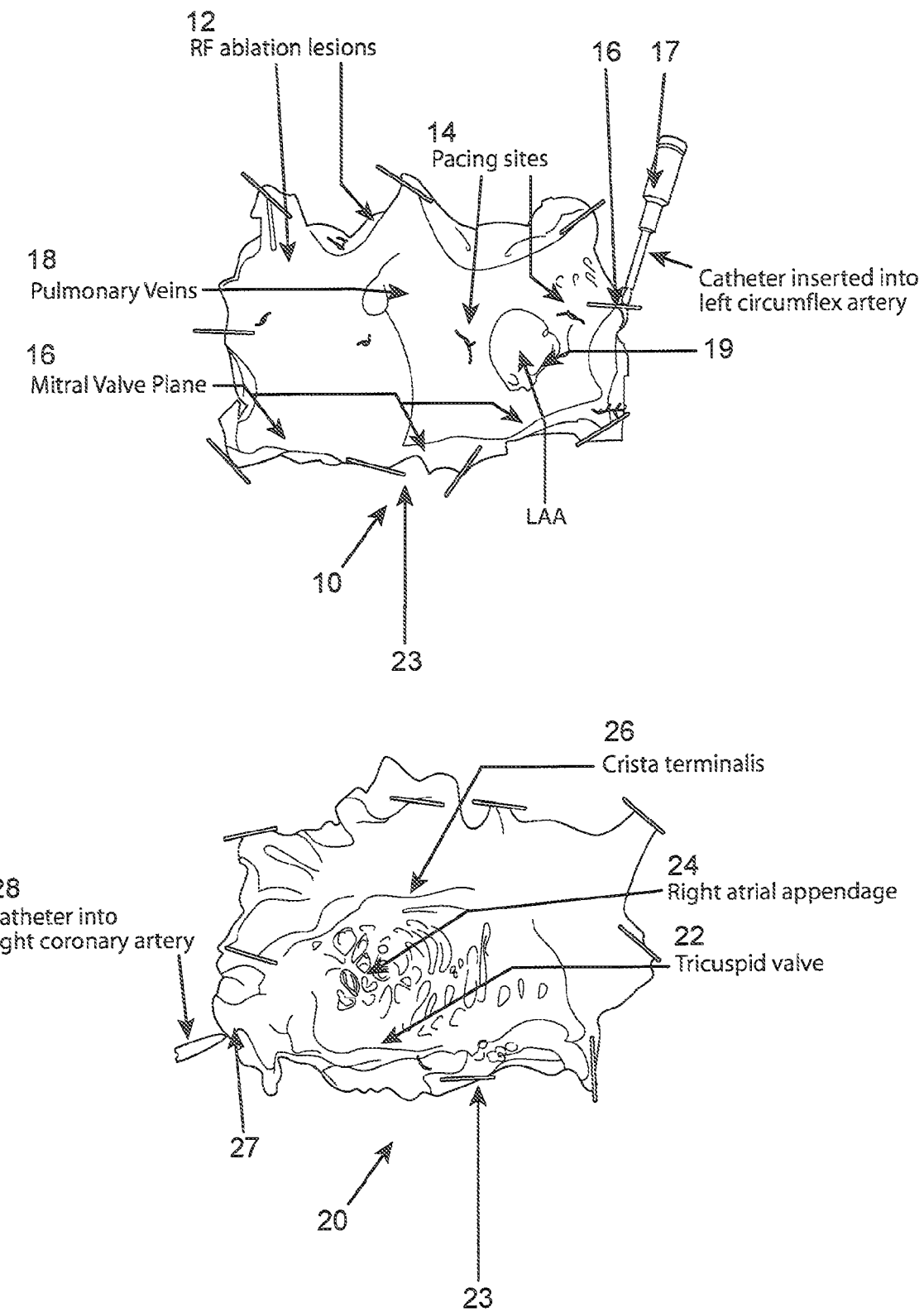
FIG. 1 illustrates a prospective view of a left atria preparation and a right atria preparation mounted to an electrode plaque in a bath with the epicardial surface facing down.

Referring now to FIG. 1, the isolated left atria is generally indicated by numeral 10 and the right atria is generally indicated by numeral 20. In the right atria 20, there were fourteen experimental preparations (n=14), the atrium was dissected from the rest of the heart and divided through the superior venae cava down to the inferior vena cava to facilitate mounting of the tissue on the electrode plaque 23. The right coronary artery 27 was cannulated with a catheter 28, e.g., sixteen (16) gauge. The crista terminalis 26, the right atrial appendage 24 and the tricuspid valve 22 are also shown.

In the left atria preparations 10, there were six experimental preparations (n=6). The heart lung block was removed, the lungs were cleanly dissected from the heart, and the pulmonary veins were divided one (1) centimeter from their insertion into the left atria 10. The ventricles and right atria 20 were excised. The circumflex artery 16 was dissected up to the aortic root and distally to beyond the last atrial branch, and all of the ventricular branches were ligated. The circumflex artery 16 was cannulated with a catheter 17, e.g., sixteen (16) gauge. The left atria 10 was divided through the right and left superior veins, unfolded, and mounted on the electrode plaque 23. The pulmonary veins 18, the mitral valve plane 16, pacing sites 14, releasing factor ablation lesions 12, and the left atria area 19 are also shown.

Before the isolated atrial preparations 10, 20 were mounted to the electrode plaque 23 in a bath; the appendages were ablated using bipolar radiofrequency energy. An illustrative example of this type of device is the AtriCure™ ablation and sensing unit with associated hand piece manufactured by AtriCure Inc., having a place of business at 6033 Schumacher Park Drive, Cincinnati, Ohio 45069. The hand piece or clamp created transmural lesions (less than one (1) millimeter wide) that prevents electrical conduction across the lesion. The epicardial surface was mounted on a flat electrode platform containing two hundred and fifty-six (256) unipolar electrodes with an interelectrode distance of five (5) millimeters. The atrial appendage of each preparation was placed into a slot in the electrode template that allowed the atrium to lie flat.

In this illustrative, but nonlimiting experiment, the isolated atrial preparations 10, 20 were kept in a temperature-controlled bath at 37° C. and perfused with a Krebs-Henseleit ("KH") solution at a rate of 8 to 10 mL/min (~50 mm Hg). The composition of the KH solution was as follows (mm/L): $Na^+$, 143; $K^+$, 4.7; $Cl^-$, 128; $Ca^{2+}$ 1.25, $HCO^{3-}$, 25; $Mg^{2+}$, 1.2; and dextrose, 11.1. The solution was oxygenated with 95% $O_2$ and 5% $CO_2$ (pH=7.4). The preparations were continuously superfused with KH as shown in FIG. 1.

As shown in FIG. 1, pacing sites 14 were marked such that pacing was always performed from the same sites 14. Pacing was conducted at 1.5 times the pacing threshold. The $S_1S_1$ interval used for all of the pacing was 300 milliseconds. The effective refractory period ("ERP") was determined at each pacing site by incrementally decreasing the $S_1S_2$ interval by five (5) milliseconds until capture no longer occurred. The effective refractory period was defined as the shortest $S_1S_2$ interval that captured the atrium. In general terms, the effective refractory period is the period that follows effective stimulation, during which excitable tissue fails to respond to a stimulus of threshold intensity. After the baseline effective refractory period values were determined, at each marked pacing site, the solution was switched to KH solution with acetylcholine at a concentration of $10^{-3.5}$ M.[12]

Figure 2:
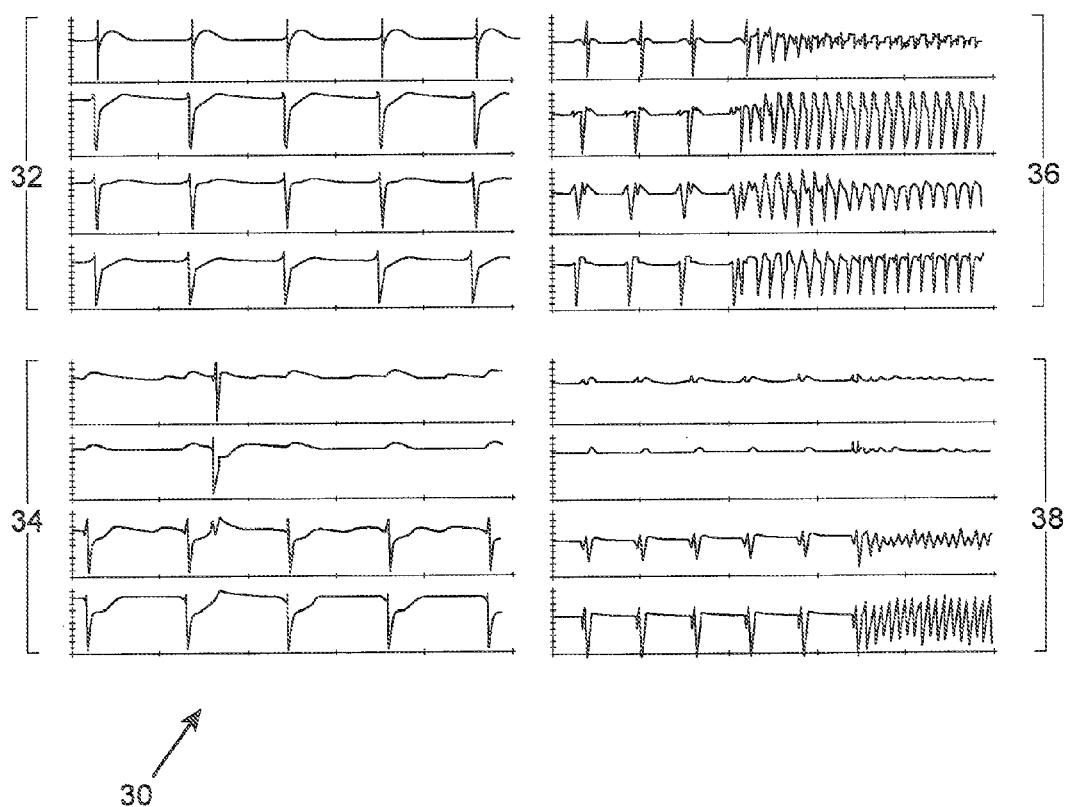
FIG. 2 illustrates an exemplary electrogram of a normal sinus rhythm, an atrial fibrillation in an entire preparation, a normal sinus rhythm in the preparation after a first ablation; divides the preparation in halves, and an atrial fibrillation in one half of the preparation after the first ablation.

Referring now to FIG. 2, the electrical activity of the atria was recorded in the form of electrograms as generally indicated by numeral 30. The first electrogram is that of a normal sinus rhythm ("NSR") as indicated by numeral 32. If the preparation continuously fibrillated for more than 30 seconds, it was considered a sustained episode of atrial fibrillation shown in the second electrogram indicated by numeral 36. The perfusion solution was then switched to KH alone until the arrhythmia terminated. The radiofrequency bipolar ablation device was used to divide the arrhythmogenic sections of the preparation. The effective refractory periods were again recorded at all of the pacing sites 14, as shown in FIG. 1, with and without acetylcholine, which is the third electrogram indicated by numeral 34 in FIG. 2. Any section that maintained an arrhythmia after the first ablation was subsequently divided again which is the fourth electrogram indicated by numeral 38 in FIG. 2. The effective refractory periods were again determined with and without acetylcholine. This process continued until all of the sections no longer maintained an arrhythmia.

Figure 3:
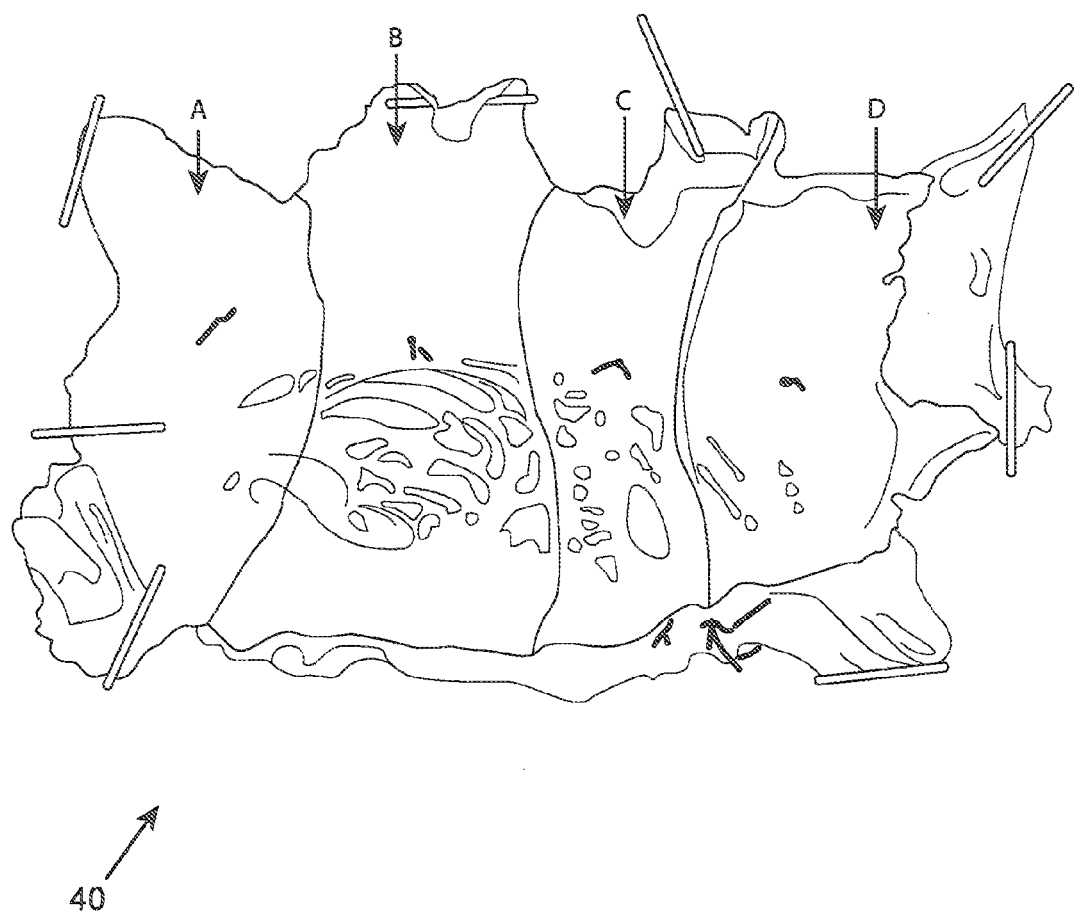
FIG. 3 illustrates a prospective view of an atrial preparation after completion of the study where all ablation lesions are complete.

At the conclusion of the illustrative, but nonlimiting, experiment, a lissamine green dye bolus was injected into the preparation to ensure that there were no perfusion abnormalities. Any sections of the atrium that were not well perfused were excluded from the data analysis. The atrial sections were photographed with a high-resolution digital camera and permanently fixed in a ten percent (10%) buffered formalin. The digital photos were analyzed to determine the minimum and maximum tissue height; the minimum, maximum, and average tissue width; and the area of all tissue sections created, which is generally indicated in FIG. 3 by numeral 40. The fixed atrial sections were then dissected, and only atrial myocardium was weighed. Illustrative, but nonlimiting software that can analyze digital images includes Scion Image™, which is manufactured by the Scion Corporation, having a place of business at 82 Worman's Mill Court, Suite H, Frederick, Md. 21701 and Adobe Photoshop™, manufactured by Adobe Systems Incorporated, having a place of business at 345 Park Avenue, San Jose, Calif. 95110-2704.

The electrograms recorded during pacing at 300 milliseconds were analyzed to calculate the activation sequence and the conduction velocities.[14] The mean, maximum, and minimum conduction velocities ("CVs") and standard deviations ("SDs") for each section were then calculated. Wavelength was calculated as the product of the average conduction velocity and the effective refractory period of each section of the atrium.[8]

Figure 12:
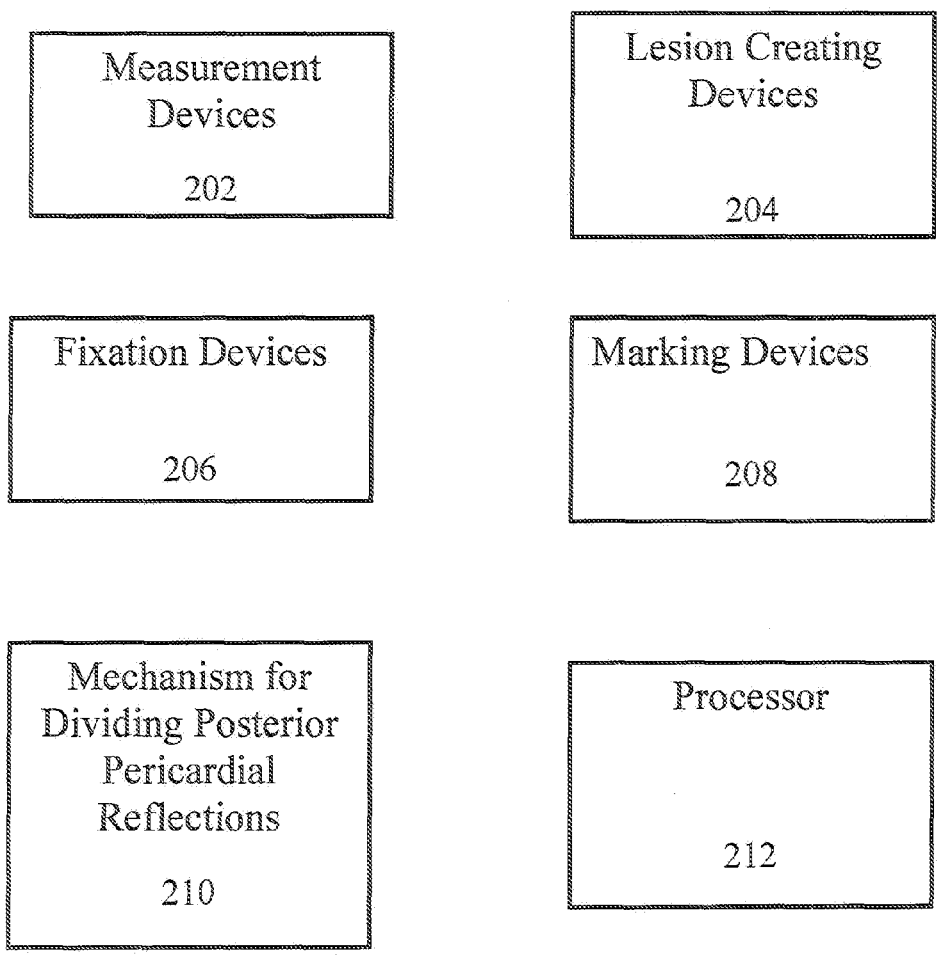
FIG. 12 is a labeled box representation of components of the system.

All of the data developed in these illustrative, but nonlimiting experiments, were expressed as plus or minus standard deviation (±SD). Analysis of variance with multiple comparisons was used for comparisons of more than two (2) groups. Multiple comparisons were made with a post hoc test, e.g., Fishers lysergic acid diethylamide. A multivariable logistical regression was performed to develop a model for the associations among the probability of atrial fibrillation, effective refractory period, and tissue area. A probability of greater than five percent (5%) (P<0.05) was considered statistically significantly different. An illustrative, but nonlimiting, example of software that can perform this analysis includes SYSTAT®, manufactured by Systat Software, Inc., having a place of business at 501 Canal Blvd, Suite E, Point Richmond, Calif. 94804-2028. Mathematical analysis performed with the present invention utilizes a processor 212, as shown in FIG. 12.

Referring now to FIG. 4, the results of the analysis of the tissue geometry for the left atria and right atria is generally indicated by numeral 50. There is a column for variables 52, a column for data involving the right atria 54, a column for data for the left atria 56 and a column for the "P value" 58 which is a P value to provide a probability that replication of the experiment would yield the same conclusion. The first variable is the tissue surface area 60, the second variable is the tissue weight 62, the third variable is the maximum tissue width 64, the fourth variable is the minimum tissue width 66, the fifth variable is the average tissue width 68, the sixth variable is the maximum tissue height 70 and the seventh variable is the minimum tissue height 72.

For each of the variables 60, 62, 64, 66, 68, 70 and 72 there is a measured value with both a plus and minus standard deviation in the column of data for the right atria 54, the column of data for the left atria 56 and the column of data for the "P value" 58 to provide a probability that replication of the experiment would yield the same conclusion.

Referring now to FIG. 5, the results of the analysis of the effective refractory period, conduction velocity and wavelength in the left atria and right atria are generally indicated by numeral 80. There is a column for variables 88, a column for data involving the right atria 82, a column for data for the left atria 84 and a column for the "P value" 86 which is a P value to provide a probability that replication of the experiment would yield the same conclusion.

There a first category in the variables column 88 that is "whole preparation" 90, which refers to either the left atria and right atria before any ablations were performed, that is, the atrium in its entirety. Under this general category variable 90 is a first variable 92, which is the effective refractory period without any acetylcholine ("AC") and a second variable 94, which is the effective refractory period with acetylcholine ("AC").

There a second category in the variables column 88 that is "all sections combined" 96. The term "all sections" is used to describe an analysis performed when all of the varying sized sections, including the whole, were combined for that test. Under this general category variable 96 is a third variable 98, which is the effective refractory period without any acetylcholine ("AC") and a fourth variable 100, which is the effective refractory period all sections combined with acetylcholine ("AC"). Under this general category variable 96 is a fifth variable 102 for conduction velocity for all sections combined and a sixth variable 104, which is the standard deviation for conduction velocity. The distinction between the "whole preparation" and "all sections" allows for the differentiation of innate properties of the native atria that could be artifacts from either time in the bath or the ablative procedures.

There a third category in the variables column 88 that is again titled "whole preparation" 106, which refers to either the left atria and right atria before any ablations were performed, that is, the atrium in its entirety and replicates the first category 90. Under this general category variable 106 is a seventh variable 108, which is the maximum conduction velocity ("CV") and an eighth variable 110, which is the minimum conduction velocity ("CV").

There a fourth category in the variables column 88 that is "all sections combined" 112. The term "all sections" is used to describe an analysis performed when all of the varying sized sections, including the whole, were combined for that test, which replicates the second category 96. Under this general category variable 112 is a ninth variable 114, which is the maximum conduction velocity ("CV") and a tenth variable 116, which is the minimum conduction velocity ("CV").

Under this general category variable 112 is an eleventh variable 118, which is the wavelength for all sections combined without any acetylcholine ("AC") and a twelfth variable 119, which is the wavelength for all sections combined with acetylcholine ("AC").

For each of the variables 92, 94, 98, 100, 102, 104, 108, 110, 114, 116, 118 and 119 there is a measured value with both a plus and minus standard deviation in the column of data for the right atria 82, the column of data for the left atria 84 and the column of data for the "P value" 86 to provide a probability that replication of the experiment would yield the same conclusion.

Analysis of FIGS. 4 and 5 indicates that the right atrial was significantly larger than the left atrial. However, the left atrial was significantly heavier than the right atrial. The mean maximum widths of the whole right atrial and left atrial were not statistically different.

Furthermore, as shown in FIG. 5, there were no differences between the left and right whole atria effective refractory periods in the absence of acetylcholine. When acetylcholine was added, the mean effective refractory periods in the whole right artia was significantly less than the whole left atria. When both the right atria and the left atria sections were analyzed in the absence of acetylcholine, the right atria was found to have significantly shorter effective refractory periods than the left atria. There would appear to be no difference in the effective refractory periods ERP for all of the sections between the right and the left in the presence of acetylcholine.

The impact of the ablations on the effective refractory period was evaluated. Without acetylcholine, the effective refractory periods for the right atria trended toward decreasing values with each additional ablation (P=0.077). This trend was not observed in the left atria (P=0.278). With the addition of acetylcholine, the effective refractory period in the right atria significantly increased over time from the beginning of the experiments to the end (25.91 milliseconds±10.49 milliseconds to 42.35 milliseconds±21.58 milliseconds; P<0.001). There was no change in the effective refractory periods of the left atrial preparation over time (P=0.130) with the addition of acetylcholine.

All of the conduction velocities were calculated at a paced cycle length of 300 milliseconds. An analysis of all sections combined found no significant difference in mean conduction velocities for those sections that were perfused with acetylcholine and those that were not (P=0.476). Examination of each atrium individually and all of its conduction velocity parameters showed no difference between the average minimum conduction velocity, the average maximum conduction velocity, or the mean conduction velocity when comparing the whole right atria preparation perfused with and without acetylcholine. The average maximum conduction velocity and the overall mean conduction velocity were unchanged in the left atria whole preparation with and without acetylcholine present.

The right atria and the left atria preparations were compared for differences in minimum, maximum, and mean conduction velocity values and their standard deviations. There was a significant difference in the mean conduction velocity for all of the data points collected in the whole section, with the left atria having a faster mean conduction value than the right atria. The standard deviations for the measurement of mean conduction velocities in all of the sections were also significantly different, with the right atria having a greater standard deviation than the left atria. The maximum conduction velocities in the whole atrial preparations were greater in the right than the left. However, when the maximum conduction velocity values were examined in all of the sections, there was no significant difference. The minimum conduction velocities were significantly less in the right atria than the left atria in the whole atrial preparations and when all of the sections were combined. When the conduction velocities were analyzed in relation to ablations, there was no change in the right atria (P=0.485) or the left atria (P=0.320). The standard deviations for this evaluation were also not statistically different (right atria, P=0.204; left atria, P=0.129).

The mean wavelength was calculated by multiplying the mean conduction velocity by the effective refractory period. When the mean wavelengths without acetycholine were compared among all of the sections, there was a significant difference between the left atria and the right atria, with the right atria having a shorter mean wavelength. The comparison of mean wavelengths in the presence of acetycholine provided no statistical difference. There was no change over time when the mean wavelengths for all of the sections were pooled and compared after each ablation (P=0.508). Also, there was found to be no change in the wavelength after each ablation when each atrium was analyzed individually (right atria, P=0.595; left atria, P=0.945).

The probability of atrial fibrillation was analyzed with a univariable logistical regression being presented in FIG. 8 as generally indicated by numeral 140. There is a first column for associated variables 142, a second column for P values 144, which provide a probability that replication of the experiment would yield the same conclusion, a third column for McFadden Rho squared values 146, a fourth column for a constant coefficient 147, a fifth column for a variable coefficent 148 and a sixth column for N 150, which is the total number for each variable.

The variables under the variable column 142 include effective refractory period 152, wavelength 154, tissue area 156, tissue weight 158, maximum tissue width 160, minimum tissue width 162, and average tissue width 164. Therefore, for each variable 152, 154, 156, 158, 160, 162 and 164, there were P values 144, McFadden Rho squared values 146, constant coefficient values 147, variable coeffcent values 148, and values 150 for N. The results of the univariable logistical regression McFadden Rho squared values 146 that fall between 0.2 and 0.4 are considered satisfactory.[15]

In summary, decreasing effective refractory periods (P<0.001), increasing tissue areas (P<0.001), increasing maximum and minimum tissue widths (P<0.001), increasing average tissue widths (P<0.001), increasing tissue weights (P<0.001), maximum conduction velocity (P=0.001), and decreasing wavelengths (P<0.001) were all found to be significantly associated with an increased probability of sustained atrial fibrillation, as shown in FIG. 8. The factors that did not correlate with an increasing probability of sustained atrial fibrillation were maximum tissue height (P=0.654) and minimum tissue height (P=0.154), mean conduction velocities (P=0.319) or their standard deviations (P=0.516), and minimum conduction velocities (P=0.299).

Figure 6:
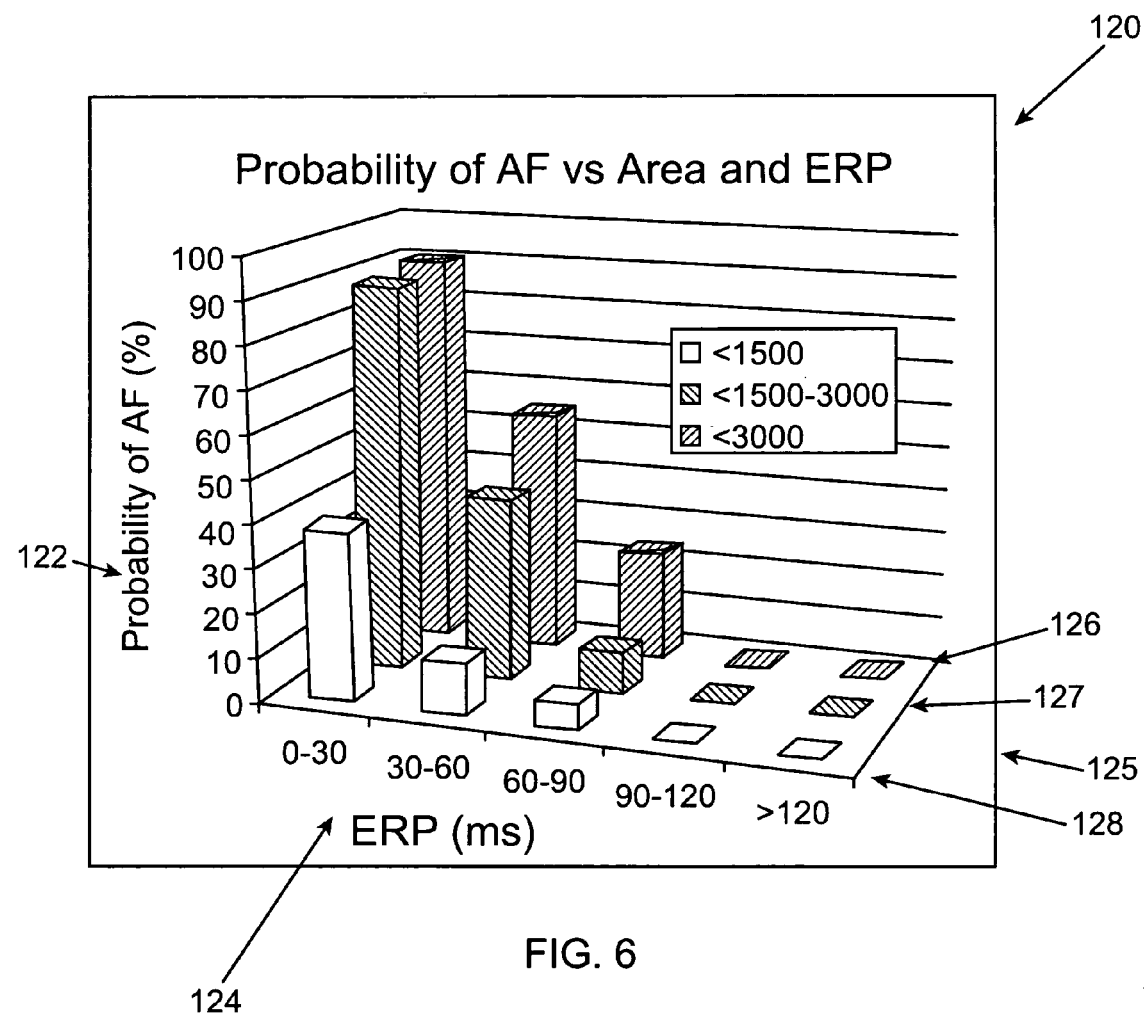
FIG. 6 illustrates a bar graph of the probability of atrial fibrillation verus tissue surface area and effective refractory period.

Referring now to FIG. 6, is a bar graph, which is generally indicated by numeral 120, showing the correlation that increased tissue area 125 and decreased effective refractory periods 124 results in an increased probability of sustained atrial fibrillation 122. The tissue area 125 is broken down into tissue area of less than 1,500 millimeters squared 128, between 1,500 millimeters squared and 3,000 millimeters squared 127 and greater than 3,000 millimeters squared 126.

Figure 7:
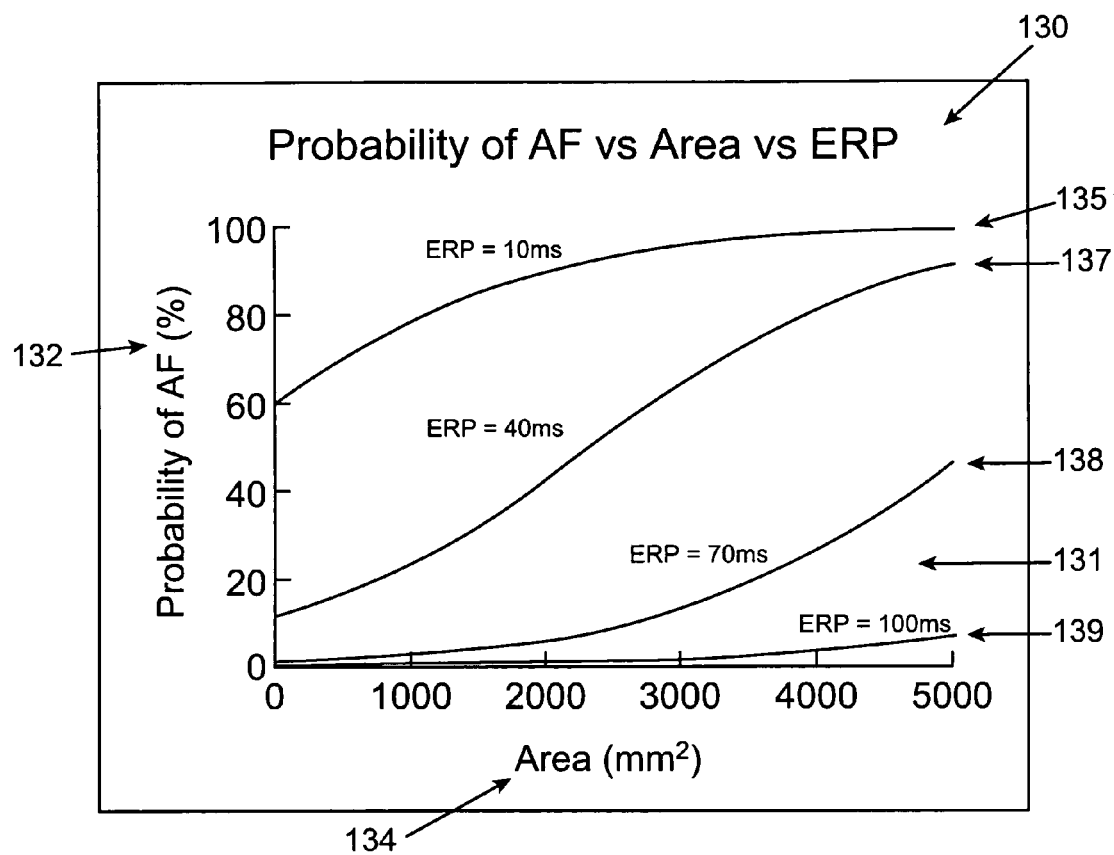
FIG. 7 illustrates a line graph of the probability of atrial fibrillation verus tissue surface area versus effective refractory period.

Referring now to FIG. 7, is a line graph, which is generally indicated by numeral 130. There are charted lines for effective refractory periods generally indicated by numeral 131. There is a line for an effective refractory period of 10 milliseconds 135, a line for an effective refractory period of 40 milliseconds 137, a line for an effective refractory period of 70 milliseconds 138 and a line for an effective refractory period of 100 milliseconds 139. This graph 130 demonstrates that with increasing tissue area 134 and decreasing effective refractory periods 131, the probability of sustained atrial fibrillation increases 132.

Figure 9:
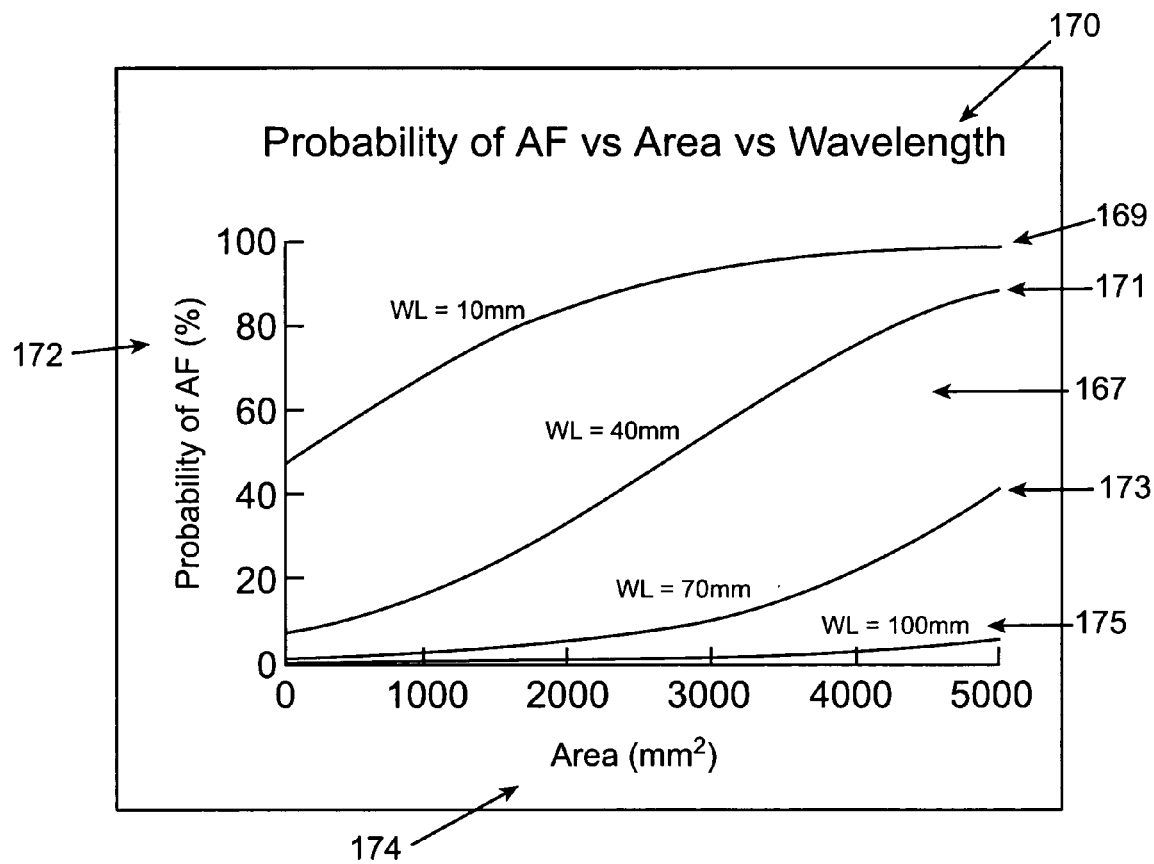
FIG. 9 illustrates a line graph of the probability of atrial fibrillation versus tissue surface area versus wavelength.

Referring now to FIG. 9, is a line graph, which is generally indicated by numeral 170. There are charted lines for wavelengths generally indicated by numeral 167. There is a line for a wavelength of 10 millimeters 169, a line for a wavelength of 40 millimeters 171, a line for a wavelength of 70 millimeters 173, a line for a wavelength of 100 millimeters 175. This graph 170 demonstrates that with increasing tissue area 174 and decreasing wavelength 167, the probability of sustained atrial fibrillation increases 172.

The overall success rate of the prior art Maze procedure is reported to be greater than ninety percent (90%). Patients with enlarged atria and those that have been in sustained atrial fibrillation for an extended period of time preoperatively have a much lower success rate.[10,11] It seems clear that there is a critical mass, above which atrial fibrillation was sustained and below which it could be prevented. By increasing tissue surface area there is a significant correlation with the probability of sustaining atrial fibrillation.

Therefore, atrial remodeling, with the increase in atrial fibrosis, can slow conduction velocity and can shorten the refractory period in atria with long-standing atrial fibrillation. The duration of preoperative atrial fibrillation is known to be a negative predictor for the success of the previously known Maze procedure.[10] The results of this investigation demonstrate the importance of the duration of the effective refractory period, with shorter effective refractory periods, the more likely it is to sustain atrial fibrillation. Multivariable logistical regression models demonstrate that increasing tissue size and decreasing effective refractory periods increase the probability of sustained atrial fibrillation, as shown in FIG. 6.

When all of the geometric data were analyzed for any correlations with atrial fibrillation, all of the variables correlated well, except for the maximum and minimum tissue heights. However, tissue height was a variable that did not vary during the experiments.

There were two types of logistical regression models utilized. Univariable logistical regression models were used to evaluate all of the parameters to determine the probability of inducing sustained atrial fibrillation. The effective refractory period and wavelength were the two variables determined to have the best fit and the greatest association with the probability of sustained atrial fibrillation. The variables: tissue area; tissue weight; maximum tissue width; minimum tissue width; and average tissue width were all deemed significant but were not determined to have as good of a fit. This demonstrates that the tissue area needed to maintain atrial fibrillation is dependent on functional factors like effective refractory period.

The variables of minimum tissue height, maximum tissue height, conduction velocity, or conduction velocity standard deviation were not significantly associated with predicting the probability of inducing sustained atrial fibrillation. This is partially due to the fact that these variables have not been modulated. This does not mean that conduction velocity is not important; it was just relatively consistent throughout the duration of the experiment. It is important to note that there was no difference between the probability of inducing sustained atrial fibrillation if the experiment occurred in the right artia or the left artia. Whereas, clinically, atrial fibrillation is often associated with the left artia, it is also known, clinically, that the refractory periods in the left artia are shorter than in the right artia. This is consistent with these experiments that show an increased probability of atrial fibrillation with a decreasing refractory period.

The multivariable logistic regression analysis combined variables and analyzed both geometric variables and physiological variables to create models for predicting the probability of inducing sustained atrial fibrillation. A series of equations was developed from these models.

Referring now to FIG. 10, which provides a table of multivariable logistical regression analysis and is generally indicated by numeral 176. This is utilized to predict the probability of a section of atria, e.g., canine, fibrillating when particular variables are entered into the equations. The first model presented utilized the variables of effective refractory period and tissue area. The data in FIGS. 6 and 7, allows for a better appreciation of the impact of effective refractory period and tissue area on the probability of inducing sustained atrial fibrillation. As the tissue area decreased and the effective refractory period increased, the probability of inducing sustained atrial fibrillation significantly decreased. However, with the same effective refractory period, as the tissue area increased, so did the probability of atrial fibrillation.

This held true for FIG. 9 that substituted wavelength for effective refractory period, and when the geometric variable was tissue weight, average tissue width, or maximum tissue width instead of tissue area. This has important relevance to the clinical problem of increasing failure rates of the previously referenced Maze technique in patients with increased atrial size and patients with longstanding atrial fibrillation and decreased effective refractory periods.

The present experiments provide correlation of the relationship between geometric and functional electrophysiological variables and the inducibility of atrial fibrillation in the atrium. In these experiments, only the tissue width and effective refractory period were modulated. Additional variables that have not been analyzed in these experiments include modifying conduction velocity as well as the height of the tissue as well as the entire intact atrium. It is believed that this analysis also is applicable to the diseased atria. No matter what the underlying pathology, the underlying substrates are still effective refractory period, conduction velocity, geometry, and premature impulse formation. As an example, in patients with persistent atrial fibrillation, the effective refractory period is decreased.

Figure 11:
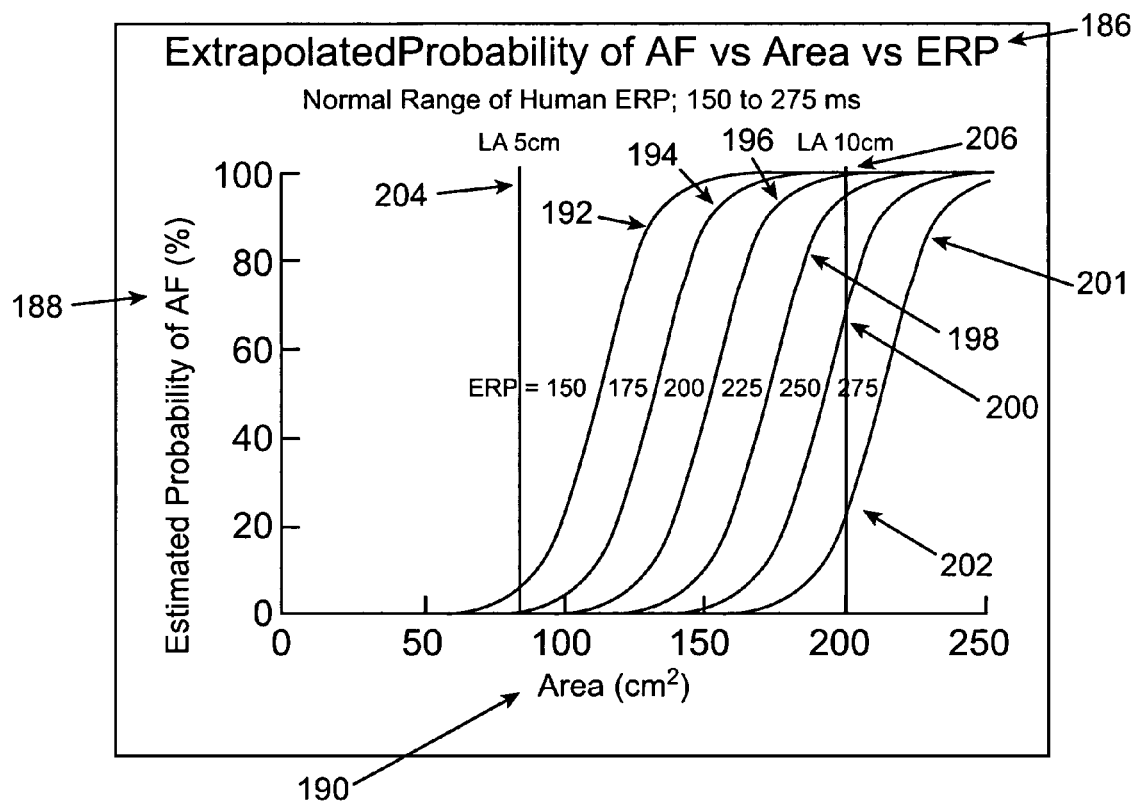
FIG. 11 illustrates a line graph of extrapolated probability of atrial fibrillation verus tissue area versus the effective refractory period.

Referring now to FIG. 11, which extrapolates the probability of atrial fibrillation versus tissue area versus effective refractory period as generally indicated by numeral 186 with altered effective refractory periods. This can include diseased tissue and can include patients with enlarged atria, who, although they have had a complete Maze procedure (including PV isolation), still have atrial fibrillation. Using this approach, it may be possible to simulate the effect of different lesion sets on the inducibility of atrial fibrillation. There are a series of lines representing effective refractory periods that are generally indicated by numeral 201. While the normal heart is in a range of 150 to 275 milliseconds for an effective refractory period, this graph 186 goes between 50 to 200 milliseconds. There is a first line for an effective refractory period of 150 milliseconds indicated by numeral 192, a second line for an effective refractory period of 175 milliseconds indicated by numeral 194, a third line for an effective refractory period of 200 milliseconds indicated by numeral 196, a fourth line for an effective refractory period of 225 milliseconds indicated by numeral 198, a fifth line for an effective refractory period of 250 milliseconds indicated by numeral 200 and a sixth line for an effective refractory period of 275 milliseconds indicated by numeral 202. These lines 192, 194, 196, 198, 200, and 202 are plotted in a correlation between tissue area in square centimeters 190 in relationship to the probability of atrial fibrillation 188. There is a first line 204 that provides an estimated atrial surface area in a heart with a right and left atrial diameter of five (5) centimeters and a second line 206 that provides an estimated atrial surface area in a heart with a right atrial diameter of five (5) centimeters and left atrial diameter of ten (10) centimeters. For each effective refractory period, as the tissue area increases 190 so does the probability of atrial fibrillation 188. There is also the possibility of simulating the effect of different lesion sets on the inducibility of atrial fibrillation.

Multiple logistic regression models demonstrated that increasing tissue size and decreasing effective refractory period increased the probability of sustained atrial fibrillation. Results from the univariable analysis showed that effective refractory period, wavelength, tissue area, tissue weight and tissue width were significantly correlated with the ability to sustain atrial fibrillation. The equation used was that the probability of atrial fibrillation AF=exp$^{(x)}$/[1+exp$^{(x)}$] where x was the constant+coefficient (variable). The multivariable logistic regression combined variables and analyzed both geometric and physiologic variables to create a model for predicting the probability of inducing sustained atrial fibrillation.

The data shown in FIG. 10, which is generally indicated by numeral 176, can be used to predict atrial fibrillation. Based on the equation, AF=exp$^{(x)}$/[1+exp$^{(x)}$] where x was the constant+coefficient (variable), the first column 178 is that for x, where x=constant+$\beta_0$ (variable 1)+$\beta_1$ (variable 2).

In the column for "X," the first equation 210 utilizes effective refractory period and tissue area as the first and second variables, respectively. The second equation 212 utilizes wavelength and tissue area as the first and second variables, respectively. The third equation 214 utilizes effective refractory period and average tissue width as the first and second variables, respectively. The fourth equation 216 utilizes effective refractory period and maximum tissue width as the first and second variables, respectively. The fifth equation 218 utilizes wavelength and maximum tissue width as the first and second variables, respectively. The sixth equation 220 utilizes effective refractory period and tissue weight as the first and second variables, respectively. Finally, the seventh equation 222 utilizes effective refractory period and maximum conduction velocity as the first and second variables, respectively. For each value of X, there is a column for P values 180, where P to provide a probability that replication of the experiment would yield the same conclusion. There is also a column for McFadden Rho Squared Values 182.

An aspect of the present invention is to utilize tissue area, effective refractory period, and conduction velocity in order to design a procedure that would make it impossible for the atrium to fibrillate. Preferably, these variables would be obtained preoperatively. Either non-invasive or invasive electrophysiologic procedures can be utilized to obtain effective refractory period and conduction velocity. Atrial surface area will be obtained using either multidetector high resolution computerized axial tomography ("CAT") scanning or magnetic resonance imaging ("MRI").These types of measurements devices are generally indicated by numeral 202 in FIG. 12.

Therefore, by using the previously described logistic regression analysis, a set of lesions could be designed with computer assistance that would make the atria fibrillation-proof. Thus, the procedure would be guided solely by geometry and the electrophysiologic properties of the tissue. This image-guided intervention would be customized based on the electrophysiologic characteristics of the atrial fibrillation in each individual patient.

This would be an image-guided, electrophysiologically-customized procedure that is preferably minimally invasive. This could include transvenous or port access, either off or on bypass. Also, there would be a series of carefully defined linear lesions across the left atria and right atria.

For providing the lesions, a number of different energy technologies could be utilized such as radio frequency, microwave, laser, ultrasound, thermal, chemical, mechanical, or cryogenic. Preferably, this would be a linear that creates long lesions. A nonlimiting, but illustrative, example of technology utilized to create lesions is disclosed in U.S. Pat. No. 6,932,813, which issued to Thompson, et al. on Aug. 23, 2005, which is incorporated herein by reference in its entirety. Another nonlimiting, but illustrative, example of technology utilized to create lesions with a catheter is disclosed in U.S. Pat. No. 6,663,622, which issued to Foley et al. on Dec. 16, 2003, which is incorporated herein by reference in its entirety. However, standard surgical techniques can also be utilized, such as scalpels in addition to the use of catheter-based techniques. These types of lesion creating devices are generally indicated by numeral 204 in FIG. 12.

It would be important to know the precise location of each lesion in order to replicate the geometry specified by the computational analysis. In order to do this, any device would have to be firmly fixed to the atrial epicardium. Preferably, this fixation mechanism would be a unipolar device. It is proposed that suction be used to fix the device to the epicardial surface. Other fixation methods include suture, clamping or balloon inflation. This would allow for the precise geometrical creation of lesions. Another nonlimiting, but illustrative, example of technology utilizing suction assisted ablation device having a support surface is disclosed in U.S. Pat. No. 6,558,382, which issued to Jahns et al. on May. 6, 2003, which is incorporated herein by reference in its entirety. These types of fixation devices are generally indicated by numeral 206 in FIG. 12.

Another aspect of the present invention is an ablation device that incorporates a marking mechanism to delineate the precise lesion width. The marking mechanism is proposed to be a dye that would be infused through the device to make it clearly visible to the observer. Other marking devices include clips, absorbable strips, felt, staples, and so forth. Another nonlimiting, but illustrative, example of technology utilizing marking dye is disclosed in U.S. Pat. No. 6,669,694, which issued to Shadduck on Dec. 30, 2003, which is incorporated herein by reference in its entirety. These types of fixation devices are generally indicated by numeral 208 in FIG. 12.

Finally, another aspect of the present invention is a device to divide the posterior pericardial reflections. This device could include a deflectable handle that could retract the heart and either a cautery, ultrasound or scissors device to divide the pericardium. A nonlimiting, but illustrative, example of technology utilized to retract heart tissue is disclosed in U.S. Pat. No. 5,613,937, which issued to Garrison et al. on Mar. 25, 1997, which is incorporated herein by reference in its entirety. These types of mechanism for dividing posterior pericardial reflections are generally indicated by numeral 210 in FIG. 12.

As is evident from the foregoing description, certain aspects of the present invention are not limited by the particular details of the examples illustrated herein, and it is therefore contemplated that other modifications and applications, or equivalents thereof, will occur to those skilled in the art. The terms "have," "having," "includes" and "including" and similar terms as used in the foregoing specification are used in the sense of "optional" or "may include" and not as "required." Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims that follow.

BACKGROUND REFERENCES

[1]Go A S, Hylek E M, Phillips K A, Chang Y, Henault L E, Selby J V, Singer D E. Prevalence of diagnosed AF in adults: national implications for rhythm management and stroke prevention: the AnTicoagulation and Risk Factors In AF (ATRIA) Study. *JAMA*. 2001;285:2370-2375.

[2] Garrey W. The nature of fibrillary contraction of the heart: its relation to tissue mass and form. *Am J Physiol.* 1914; 33:397-414.

[3] Lewis T. *The Mechanisms and Graphical Registration of the Heart Beat,* 3rd ed. London, United Kingdom: Shaw and Sons; 1925.

[4] Moe G K. On the multiple wavelet hypothesis of AF. *Arch Int Pharmacodyn Ther.* 1962; 140:183-188.

[5] Moe G K, Rheinboldt W C, Abildskov J A. A computer model of AF. *Am Heart J.* 1964;67:200-220.

[6] Allessie M A, Lammers W J E P, Bonke F I M, Hollen J. Experimental evaluation of Moe's multiple wavelet hypothesis of A F. In: Zipes D P, Jalife J, eds. *Cardiac Electrophysiology and Arrhythmias*. New York, N.Y.: Grume & Stratton; 1985:265-275.

[7] Kennings K T, Kirchhoff C J, Smets J R, Wellens H J, Penn O C. Alesse M A. High-density mapping of electrically induced AF in humans. *Circulation.* 1994; 89:1665-1680.

[8] Weiner N, Rosenbluth A. The mathematical formulation of the problem of conduction of impulses in a network of connected excitable elements, specifically in cardiac muscle. *Arch Inst Cardiol Mex.* 1946; 16:205-265.

[9] Cox J L, Schuessler R B, Boineau J P. The development of the maze procedure for the treatment of AF. *Semin Thorac Cardiovasc Surg.* 2000; 12:2-14.

[10] Gaynor S L, Schuessler R B, Bailey M S, Ishii Y, Boineau J P, Gleva M J, Cox J L, Damiano R J. Surgical treatment of AF: predictors of late recurrence. *J Thorac Cardiovasc Surg.* 2005; 129:104-111.

[11] Kosakai Y. Treatment of AF using the maze procedure: the Japanese experience. *Semin Thorac Cardiovasc Surg.* 2000; 12:44-52.

[12] Schuessler R B, Grayson T M, Bromberg B I, Cox J L, Boineau J P. Cholinergically mediated tachyarrhythmias induced by a single extrastimulus in the isolated canine RA. *Circ Res.* 1992; 71:1254-1267.

[13] Doshi R N, Wu T J, Yashima M, Kim Y H, Ong J J C, Cao J M, Hwang C, Yashar P, Fishbein M C, Karagueuzian H S, Chen P S. Relation between ligament of marshall and adrenergic atrial tachyarrhythmia. *Circulation.* 1999; 100:876-883.

[14] Bayly P V, KenKnight B H, Rogers J M, Hillsley R E, Ideker R E, Smith W M. Estimation of conduction velocity vector fields from epicardial mapping data. *IEEE Trans Biomed Eng.* 1998; 45:563-571.

[15] Hensher D, Johnson L W. *Applied Discrete Choice Modeling*. London, United Kingdom: Helm; 1981.

[16] Prasad S M, Maniar H S, Camillo C J, Schuessler R B, Boineau J P, Sundt T M, Cox J L, Damiano R J. The Cox maze III procedure for AF: long-term efficacy in patients undergoing lone versus concomitant procedures. *J Thorac Cardiovasc Surg.* 2003; 126:1822-1827.

[17] Falk R H. AF. *N Engl J. Med.* 2001; 344:1067-1077.

[18] Falk R H. Etiology and complications of AF: insights from pathology studies. *Am J Cardiol.* 1998; 82:10N-17N.

The invention claimed is:

1. A method for treating atrial fibrillation comprising:
    obtaining at least one measurement with a measurement device associated with an atria selected from the group consisting of effective refractory period, wavelength, tissue surface area, tissue weight, maximum tissue width, minimum tissue width, average tissue width, conduction velocity and maximum conduction velocity;
    performing a multivariable logistic regression analysis, with a processor, to determine atrial tissue section areas that will prevent atrial fibrillation;
    designing a set of lesions based on probabilities generated from the multivariable logistic regression analysis that provided the atrial tissue section areas;
    creating the designed lesions with a cutting or ablation device to obtain the atrial tissue section areas in order to significantly reduce the probability of sustained atrial fibrillation, wherein the multivariable logistic regression analysis includes the equation for determining atrial fibrillation being:
    $AF = \exp^{(x)}/[1+\exp^{(x)}]$ where $x = \text{constant} + \beta_0$ (variable 1) $+ \beta_1$ (variable 2) and x is selected from the group consisting of effective refractory period, wavelength, tissue area, tissue weight, maximum tissue width, minimum tissue width, average tissue width, conduction velocity and maximum conduction velocity and $\beta_0$ and $\beta_1$ are constants; wherein AF is the probability of atrial fibrillation so that if an acceptable probability of atrial fibrillation is utilized, a value for the variable 1 and the variable 2 can be determined.

2. The method for treating atrial fibrillation as set forth in claim 1, wherein the step of obtaining at least one measurement with a measurement device associated with an atria selected from the group consisting of effective refractory period, wavelength, tissue surface area, tissue weight, maximum tissue width, minimum tissue width, average tissue width, conduction velocity and maximum conduction velocity includes utilizing computerized axial tomography scanning or magnetic resonance imaging.

3. The method for treating atrial fibrillation as set forth in claim 1, wherein the creating lesions with a cutting device in the locations of the secured atrial epicardium to treat atrial fibrillation includes utilizing a mechanism selected from the group consisting of cutting devices that include a device that utilizes radio frequencies, a device that utilizes microwaves, a laser, a device that utilizes ultrasound, a device that utilizes thermal energy, a device that utilizes at least one chemical, a mechanical cutting device, or a device that utilizes cryogenics.

4. The method for treating atrial fibrillation as set forth in claim 1, further comprising marking to delineate lesion width.

5. The method for treating atrial fibrillation as set forth in claim 4, wherein the marking to delineate lesion width includes utilizing at least one dye, at least one clip, at least one absorbable strip, felt or at least one staple.

6. The method for treating atrial fibrillation as set forth in claim 1, further comprising dividing posterior pericardial reflections.

7. The method for treating atrial fibrillation as set forth in claim 6, wherein the dividing posterior pericardial reflections further includes retracting a heart with a heart retraction device.

8. The method for treating atrial fibrillation as set forth in claim 6, wherein the dividing posterior pericardial reflections further includes retracting a heart with a heart retraction device having a retractable handle.

9. The method for treating atrial fibrillation as set forth in claim 6, wherein the dividing posterior pericardial reflections includes dividing posterior pericardial reflections with a device to divide the pericardium.

10. The method for treating atrial fibrillation as set forth in claim 9, wherein the dividing posterior pericardial reflections with a device to divide the pericardium includes utilizing a cautery, an ultrasound or at least one pair of scissors.

* * * * *